United States Patent [19]

Commandeur et al.

[11] Patent Number: 4,996,360
[45] Date of Patent: Feb. 26, 1991

[54] PREPARATION OF ARYLSULFONYL (ALKYL) AMIDES

[75] Inventors: Raymond Commandeur, Vizille; Elie Ghenassia, Grenoble, both of France

[73] Assignee: Atochem, Puteaux, France

[21] Appl. No.: 323,857

[22] Filed: Mar. 15, 1989

[30] Foreign Application Priority Data

Mar. 17, 1988 [FR] France ................. 8803477

[51] Int. Cl.$^5$ ......................... C07C 303/38
[52] U.S. Cl. ...................... 564/90
[58] Field of Search ........................... 564/90

[56] References Cited

U.S. PATENT DOCUMENTS 3,860,531  1/1974  Cole et al. ............ 252/426
4,713,489  12/1987 Birum et al. .......... 564/90

FOREIGN PATENT DOCUMENTS 0027906  5/1981  European Pat. Off. .
0007623  2/1980  Fed. Rep. of Germany .
1430882  4/1976  United Kingdom .

OTHER PUBLICATIONS

Methoden der Organischen Chemie, George Thieme Verlag, Stuttgart, vol. 9, (1955), pp. 609–610.
Müller et al., *Methoden Der Organischen Chemie*, George Thieme Verlag, Stuttgart, vol. 9 (1955), pp. 609–610.

*Primary Examiner*—Richard L. Raymond
*Assistant Examiner*—Peter G. O'Sullivan
*Attorney, Agent, or Firm*—Burns, Doane, Swecker & Mathis

[57] ABSTRACT

The arylsulfonyl(alkyl)amides, notably N-(n-butyl)benzenesulfonamide, well adopted as heat-stable plasticizers for polyamides, e.g., nylon 11 and nylon 12, are directly prepared by (a) intimately contacting an arylsulfonyl halide with a stoichiometric excess of both an alkylamine and an alkaline agent, with the alkaline agent being present in aqueous solution, (b) eliminating water and excess alkylamine from the organic phase produced in stage (a), and (c) separating final product arylsulfonyl(alkyl)amide from the residual organic phase remaining after stage (b).

10 Claims, No Drawings

PREPARATION OF ARYLSULFONYL (ALKYL) AMIDES

BACKGROUND OF THE INVENTION

1. Field of the Invention:

The present invention relates to the preparation of arylsulfonyl(alkyl)amides, and, more especially, to the preparation of arylsulfonyl(alkyl)amides by contacting an arylsulfonyl halide with a stoichiometric excess of an alkylamine in the presence of an aqueous solution of excess alkaline agent.

2. Description of the Prior Art:

The arylsulfonyl(alkyl)amides are known compounds that are useful as plasticizers for the polyamides, in particular for the nylons 11 and 12. It is important that these plasticizers not be susceptible to degradation by heat. The plasticizer is incorporated at a high temperature (200° to 250° C.), and, in use, must not be a source of formation of acid products, which present the risk of developing objectionable coloration. Such acid products can also adversely affect the mechanical properties of the polymers (chain rupture).

European Patent Application EP 7623, published Feb. 6, 1980, describes a process for the purification of arylsulfonyl(alkyl)amides by the action of an alkaline agent at 200° C. to obtain a heat-stable compound.

SUMMARY OF THE INVENTION

Accordingly, a major object of the present invention is the provision of an improved process for the preparation of heat-stable arylsulfonyl(alkyl)amides which are directly usable as plasticizers for the polyamides, and which improved process conspicuously avoids the requirement for product purification to date characterizing the state of this art (EP 7623).

Briefly, the present invention features a process for the synthesis of arylsulfonyl(alkyl)amides having the formula:

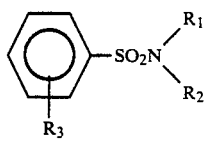

wherein $R_1$ is a hydrogen atom or an alkyl radical having from 1 to 10 carbon atoms, $R_2$ is an alkyl radical having from 1 to 10 carbon atoms and $R_3$ is one or more identical or different substituents selected from among hydrogen atoms or halogen atoms and alkyl radicals having up to 5 carbon atoms, comprising:

(a) contacting an arylsulfonyl halide with a stoichiometric excess of an alkylamine and an aqueous solution of an alkaline agent, the amount of alkaline agent being in stoichiometric excess relative to the arylsulfonyl halide;

(b) eliminating water and unreacted alkylamine from the organic phase produced in stage (a); and (c) separating final product arylsulfonyl(alkyl)-amide from the residual organic phase remaining after stage (b).

DETAILED DESCRIPTION OF THE PREFERRED EMBODIMENTS OF THE INVENTION

More particularly according to the present invention, although $R_1$ and $R_2$ may be different, it is advantageous to use starting materials in which $R_1$ and $R_2$ are identical. Preferred are those compounds in which $R_1$ and $R_2$ have no more than 3 carbon atoms. Other preferred compounds are those in which $R_1$ is hydrogen and $R_2$ is an alkyl radical advantageously having from 2 to 6 carbons and preferably 4 carbon atoms.

Preferred substituents for the benzene nucleus are fluorine, chlorine, bromine and methyl. The nucleus may have several of these substituents simultaneously, for example, there may be one methyl substituent and one or more bromine atom substituents, or one methyl substituent and one or more chlorine atom substituents. Particularly advantageous compounds are those in which $R_3$ is hydrogen, that is to say, an unsubstituted benzene nucleus, $R_1$ is also hydrogen and $R_2$ is an alkyl radical having from 2 to 6 carbon atoms.

A preferred final product is N-(n-butyl)benzene-sulfonamide of the formula:

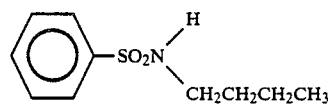

The starting material arylsulfonyl halide is a compound of the following formula:

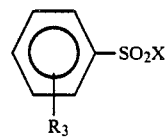

in which $R_3$ is as defined above, and X designates a halogen atom. X is advantageously chlorine or bromine, and preferably chlorine.

The starting material alkylamine is a compound of the following formula:

in which $R_1$ and $R_2$ are as defined above.

The reaction between the arylsulfonyl halide and the alkylamine is essentially complete and, in theory, it requires one mole of halide for one mole of amine, one mole of HX being produced which is neutralized (converted) by means of the alkaline agent.

It is preferred to use benzenesulfonyl chloride, i.e., that compound in which $R_3$ is hydrogen and X is chlorine, and n-butylamine, i.e., that compound in which $R_1$ is hydrogen and $R_2$ is n-butyl.

In stage (a) it is essential to use a stoichiometric excess of alkylamine, namely, more than one mole of amine is used per one mole of halide.

This excess is advantageously 20%, in moles, that is to say, 1.2 moles of amine per one mole of halide employed, and preferably 5 to 15%. The use of a large excess would not be a departure from the scope of the invention, but would necessitate recycling large quantities of amine upon completion of the reaction.

Alkali metal or alkaline earth metal hydroxides, carbonates, bicarbonates and alcoholates, for example, are advantageously used as the alkaline agent in aqueous solution. It is preferred to use sodium hydroxide (soda) or potassium hydroxide and, more preferably, sodium hydroxide. Although the concentration of the sodium or potassium hydroxide is not critical, it is convenient to use aqueous solutions having concentrations of from 10% to 30% by weight. The necessary amount of alkaline agent is a function of the amount of sulfonyl halide employed in (a), the stoichiometric amount being one equivalent of alkaline agent per one mole of sulfonyl halide, that is to say, if sodium or potassium hydroxide is used, at least one mole is required for one mole of sulfonyl halide. An excess of alkaline agent must be used, relative to the stoichiometric amount described above. It is advantageous to use a molar excess of up to 10% and preferably from 1% to 5%. The use of a large excess of sodium hydroxide also would not be a departure from the scope of the invention, but the process would be complicated by the large amounts of excess product to be eliminated.

The operation may be continuous or discontinuous and the arylsulfonyl halide, alkylamine and aqueous solution of alkaline agent may be added in any order, or partly in one order and partly in another. The only condition to be observed is that the arylsulfonyl halide must not be destroyed by reaction with the alkaline agent. The arylsulfonyl halide may, for example, be contacted with the alkylamine before adding the alkaline agent. The arylsulfonyl halide may also be introduced into a stirred mixture of alkaline agent in aqueous solution and alkylamine. The expression "stirred mixture" is used because the alkaline solution and the alkylamine are not generally miscible, and a type of unstable emulsion is formed by stirring. According to another embodiment of the invention, the arylsulfonyl halide and aqueous solution of alkaline agent may also be introduced into the alkylamine, with a slight delay for the alkaline solution. Such "delay" is in terms of the number of moles of alkaline agent relative to the number of moles of arylsulfonyl halide.

It is essential according to the invention to establish intimate contact among the arylsulfonyl halide, the alkylamine, water and the alkaline agent. The use of an anhydrous alkaline agent and water, or an anhydrous alkaline agent and an alkylamine in aqueous emulsion, would also be within the ambit of the invention. The arylsulfonyl halide may be used as is, or in solution in a solvent; the alkylamine may also be used as is, or possibly in a solvent, for example toluene.

Although stage (a) may be carried out at any temperature and pressure, provided of course that the products are not decomposed, it is preferred to operate at or close to ambient temperature and at or close to atmospheric pressure, such that the halide is liquid and the amine is also liquid. If it is impossible to combine these conditions, a zone of temperature and pressure is selected in which the halide is liquid and the amine is gaseous. These conditions are advantageously a temperature below 150° C. and a relative pressure below 5 bars.

It is preferred to operate at atmospheric pressure and at a temperature close to room temperature, that is to say, at a temperature of from 0° to 50° C.

The duration of stage (a) is not critical, but the reaction is instantaneous and its duration is determined by the practical conditions associated with the apparatus and the amounts used.

This duration is usually on the order of 15 minutes to a few hours.

The contacting is an operation known per se and may be carried out in any apparatus used in the chemical industry; stirred apparatus is advantageously used.

When all of the reactants in this stage (a) have been brought into intimate contact, it is advantageous to maintain the stirred reaction mixture at a temperature of from 20° to 100° C., and preferably from 40° to 70°, for a period of time that may range from a few minutes to a few hours, and preferably from one hour to three hours. The reaction mixture obtained at the end of stage (a) is subsequently separated into an aqueous phase and an organic phase containing essentially all of the arylsulfonyl(alkyl)-amide, some alkylamine and a few percent of water. This separation of the two phases is an operation per se known to this art.

Stage (b) comprises eliminating the water and the alkylamine from this organic phase. This is advantageously carried out by distillation. This may be accomplished under vacuum, or up to a few bars of pressure, so long as the temperature does not exceed that at which the organic phase begins to degrade, or to produce colored products or products of decomposition. This temperature is usually below 180 C. It is advantageous to conduct the operation at a temperature of from 130° to 170° C. To operate at a higher temperature is within the scope of the invention, but there would be a risk of degrading the products, and it is simpler to operate at a lower temperature.

The duration of the operation is also not critical; it is determined by the practical conditions associated with the apparatus and the amounts of water and alkylamine to be eliminated.

This stage (b), like all of the other stages according to the present invention, may be carried out continuously or discontinuously. When all of the water and alkylamine have been eliminated, an organic residue is obtained, containing essentially all of the desired amide. Stage (c) is carried out by any known means of separation. A distillation is advantageously used, or one or more flash evaporations, or evaporation from a film or thin layer and operating under vacuum.

In order to further illustrate the present invention and the advantages thereof, the following specific examples are given, it being understood that same are intended only as illustrative and in nowise limitative.

In said examples to follow, the heat stability test entailed maintaining the arylsulfonyl(alkyl)amide for 3 hours at 250° C. under nitrogen; the color at the end of the test must be less than 250 Hazen. Such a product may then be used as a plasticizer.

Unless otherwise indicated, the operation was carried out in a glass reactor equipped with a stirrer, a thermometric jacket, an injector for purging with nitrogen, a vertical condenser and cooling by cold water or brine bath. The materials were blanketed under nitrogen during the distillations (stages (b) and (c)).

EXAMPLE 1:

(a) 3 moles of benzenesulfonyl chloride ($C_6H_5SO_2Cl$) were introduced over the course of 1 hour and 30 minutes into a mixture containing 3.051 moles of sodium hydroxide (as an aqueous solution at a concentration of 19.37% by weight) and 3.3 moles of n-butylamine (CH₃CH₂CH₂CH₂NH₂). The temperature of the reactor was maintained at 20° C. Then the temperature was increased to from 60° to 65° C. for 2 hours. After phase separation, 675 g of an organic phase were obtained containing 3×0.9959 moles of N-(n-butyl)benzenesulfonamide (C₆H₅SO₂NHCH₂CH₂CH₂CH₃) (BBSA).

(b) The organic phase was distilled to eliminate water and n-butylamine, the temperature at the base of the column being maintained at 20° to 145° C. under a vacuum of 740 to 10 mm Hg for 1 hour.

(c) The residue obtained was distilled under vacuum (0.5 mm Hg) and 96% of the BBSA contained in the organic phase at the end of stage (a) was thus collected. The heat test evidenced a color of 50 Hazen.

EXAMPLE 2:

The procedure of Example 1 was repeated, except that the temperature was maintained at 50° C. during the addition of the benzenesulfonyl chloride. The results were identical to those in Example 1.

EXAMPLE 3:

(a) 0.6 mole of benzenesulfonyl chloride was introduced into 3.3 moles of n-butylamine, the reactor being maintained at 50° C. Then, 3.051 moles of sodium hydroxide, in the form of an aqueous solution at a concentration of 19.37% by weight, and 2.4 moles of benzenesulfonyl chloride were simultaneously introduced over the course of 1 hour and 30 minutes, the reactor being maintained at 50° C. 7 g of water were added to rinse the sodium hydroxide dropping funnel. The reactor was then heated to from 60° to 65° C. for 2 hours.

After phase separation, 669 g of an organic phase were obtained containing 3×0.9939 moles of BBSA.

(b) Distillation was carried out as in Example 1.

(c) The residue obtained was distilled under a vacuum of 0.5 mm Hg and 95% of the BBSA contained in the organic phase at the end of stage (a) was thus collected. The heat test evidenced a color of 50 Hazen.

EXAMPLE 4:

The procedure of Example 2 was repeated, except a stainless steel reactor was used, the bottom of which was made of grade 304 L and the remainder of grade 316 L. Identical results were obtained.

EXAMPLE 5:

(a) 3 moles of benzenesulfonyl chloride were introduced into 3.3 moles of n-butylamine over the course of 30 minutes; the temperature of the reactor was maintained at 50° C. Then, 3.15 moles of sodium hydroxide as a 19.91% strength aqueous solution were introduced over the course of 1 hour and 30 minutes.

The sodium hydroxide dropping funnel was rinsed with 13.5 g of water. The reactor was heated to from 60° to 70° C. for 2 hours. After phase separation, 671.8 g of an organic phase were obtained containing 3 moles of BBSA.

(b) The water and amine were distilled off as in Example 1. 6.1% of the mass treated in this stage (b) wa lost during the distillation (c) The residue obtained was distilled under vacuum (0.5 mm Hg) and 92% of the BBSA contained in the organic phase at the end of stage (a) was thus collected. The heat test evidenced a color of 175 Hazen.

EXAMPLE 6:

(a) The procedure was the same as in Example 3, except that the reactor was maintained at 20° C. instead of 50° C. during the two operations of introduction of the reactants. After phase separation, 671.8 g of an organic phase were obtained containing 3×0.998 moles of BSSA.

(b) The water and amine were distilled off as in Example 1. A loss of mass of 6.07% was observed during this distillation.

(c) The residue obtained was distilled under vacuum (0.5 mm Hg) and three fractions were collected corresponding to distillation foreruns, middles and tailings (the % are by weight)

| F1 = 4.9% |
|---|
| F2 = 84.2% |
| F3 = 7.1% |

3.8% remained in the flask (% of the mass involved in stage (c)).

The heat test on F2 evidenced a color below 50 Hazen and 100 Hazen on F1 +F2 +F3.

EXAMPLE 7:

The procedure was the same as in Example 2, except that 3.75 moles of n-butylamine were used. 702.6 g of an organic phase were obtained containing 3×0.9924 moles of BBSA. Identical results were obtained.

EXAMPLE 8:

The procedure was the same as in Example 2, except that 3.15 moles of n-butylamine were used. 659.8 g of an organic phase were obtained containing 3×0.9915 moles of BBSA. Identical results were obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an arylsulfonyl(alkyl)amide having the formula:

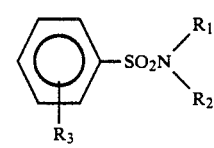

wherein $R_1$ is a hydrogen atom or an alkyl radical having from 1 to 10 carbon atoms, $R_2$ is an alkyl radical having from 1 to 10 carbon atoms, and $R_3$ is one or more hydrogen atoms or halogen atoms or lower alkyl substituents, comprising (a) intimately contacting an arylsulfonyl halide with a stoichiometric excess of both an alkylamine and an alkaline agent, said alkaline agent being present in aqueous solution, (b) eliminating water and excess alkylamine from the organic phase produced in stage (a) by distillation conducted at a temperature from 130° to 170° C., and (c) separating final product arylsulfonyl(alkyl)amide from the residual organic phase remaining after stage (b).

2. The process as defined by claim 1, comprising intimately contacting said arylsulfonyl halide with a 5% to 15% stoichiometric excess of said alkylamine.

3. The process as defined by claim 1, comprising intimately contacting said arylsulfonyl halide with a 1% to 5% stoichiometric excess of said alkaline agent.

4. The process as defined by claim 1, said alkaline agent comprising an alkali or alkaline earth metal hydroxide, carbonate, bicarbonate or alcoholate.

5. The process as defined by claim 4, said alkaline agent comprising sodium hydroxide.

6. The process as defined by claim 1, said alkaline agent being present as a 10% to 30% concentrated aqueous solution thereof.

7. The process as defined by claim 1, wherein stage (a) is carried out under stirring agitation.

8. The process as defined by claim 1, wherein stage (b) said water and excess alkylamine are eliminated by distillation.

9. The process as defined by claim 1, carried out in liquid state.

10. The process as defined by claim 1, comprising preparing N-(n-butyl)benzenesulfonamide.

* * * * *